United States Patent
Cheng et al.

(10) Patent No.: US 9,797,015 B2
(45) Date of Patent: Oct. 24, 2017

(54) GENETIC VARIANTS ASSOCIATED WITH LITHIUM RESPONSE IN BIPOLAR DISORDER

(71) Applicant: Academia Sinica, Taipei (TW)

(72) Inventors: Andrew Tai-Ann Cheng, Taipei (TW);
Yuan-Tsong Chen, Taipei (TW);
Chien-Hsiun Chen, Taipei (TW);
Chau-Shoun Lee, Taipei (TW); Ming Ta Michael Lee, Taipei (TW)

(73) Assignee: Academia Sinica, Taipei (TW)

( * ) Notice: Subject to any disclaimer, the term of this patent is extended or adjusted under 35 U.S.C. 154(b) by 6 days.

(21) Appl. No.: 14/764,448

(22) PCT Filed: Jan. 29, 2014

(86) PCT No.: PCT/US2014/013561
§ 371 (c)(1),
(2) Date: Jul. 29, 2015

(87) PCT Pub. No.: WO2014/120745
PCT Pub. Date: Aug. 7, 2014

(65) Prior Publication Data
US 2015/0361498 A1 Dec. 17, 2015

Related U.S. Application Data

(60) Provisional application No. 61/757,855, filed on Jan. 29, 2013.

(51) Int. Cl.
*C12Q 1/68* (2006.01)
*C12P 19/34* (2006.01)
*A61K 33/00* (2006.01)

(52) U.S. Cl.
CPC ............ *C12Q 1/6883* (2013.01); *A61K 33/00* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

FOREIGN PATENT DOCUMENTS

WO WO-2009/101619 8/2009

OTHER PUBLICATIONS

Andiappan (BMC Genetics. 2010. 11: 36).*
Sotos et al.; Statistics Education Research Journal, 8(2) 33-55, 2009.*
Lee, et al., "Genome-wide association study of bipolar I disorder in the Han Chinese population", Molecular Psychiatry vol. 16 pp. 548-556, 2011.
Chen, et al., "Variant GADL1 and response to lithium therapy in bipolar I disorder", The New England Journal of Medicine, vol. 370, No. 2, pp. 19-128 (e-pub Dec. 25, 2013).
Lundorf, et al., "Mutational screening and association study of glutamate decarboxylase 1 as a candidate susceptibility gene for bipolar affective disorder and schizophrenia", American Journal of Medical Genetics Part B: Neuropsychiatric Genetics, vol. 535B, No. 1, pp. 94-101 (2004).
Perlis, et al., "A genomewide association study of response to lithium for prevention of recurrence in bipolar disorder", American Journal of Psychiatry, col. 166, No. 6, pp. 718-728 (2009).
Smith, et al., "Predicting response to lithium in bipolar disorder: a critical review of pharmacogenetic studies", Journal of Mental Health, Nol. 19, No. 2, pp. 142-154 (2010).
Tighe, et al., "Predictors of lithium response in bipolar disorder" Therapeutic Advances in Chronic Disease, vol. 2, No. 3, pp. 209-226 (2011).

* cited by examiner

*Primary Examiner* — Jehanne Sitton
(74) *Attorney, Agent, or Firm* — Cesari and McKenna, LLP

(57) ABSTRACT

Described herein is a method of determining lithium responsiveness in a bipolar disorder patient. The method includes obtaining a sample from a patient having bipolar disorder, and assaying the sample for the presence or absence of one or more glutamate decarboxylase-like 1 (GADL1) gene variants selected from the group consisting of a T allele of the single nucleotide polymorphism (SNP) rs17026688, a G allele of the SNP rs17026651, and GADL1 1VS8+48delG. The presence of one or more of the GADL1 gene variants indicates that the patient is responsive to lithium treatment.

12 Claims, No Drawings

```
                              SEQUENCE LISTING

<160> NUMBER OF SEQ IDS NOS: 5

<210> SEQ ID NO 1
<211> LENGTH: 521
<212> TYPE: PRT
<213> ORGANISM: Homo sapiens
<220> FEATURE:
<221> NAME/KEY: MISC_FEATURE
<223> OTHER INFORMATION: GADL1

<400> SEQUENCE: 1

Met Ser Ser Asp Ser Asp Arg Gln Cys Pro Val Asp Gly Asp Ile Asp
1               5                   10                  15

Gln Gln Glu Met Ile Pro Ser Lys Lys Asn Ala Val Leu Val Asp Gly
                20                  25                  30

Val Val Leu Asn Gly Pro Thr Thr Asp Ala Lys Ala Gly Glu Lys Phe
            35                  40                  45

Val Glu Glu Ala Cys Arg Leu Ile Met Glu Glu Val Val Leu Lys Ala
        50                  55                  60

Thr Asp Val Asn Glu Lys Val Cys Glu Trp Arg Pro Pro Glu Gln Leu
65                  70                  75                  80

Lys Gln Leu Leu Asp Leu Glu Met Arg Asp Ser Gly Glu Pro Pro His
                85                  90                  95

Lys Leu Leu Glu Leu Cys Arg Asp Val Ile His Tyr Ser Val Lys Thr
            100                 105                 110

Asn His Pro Arg Phe Phe Asn Gln Leu Tyr Ala Gly Leu Asp Tyr Tyr
        115                 120                 125

Ser Leu Val Ala Arg Phe Met Thr Glu Ala Leu Asn Pro Ser Val Tyr
    130                 135                 140

Thr Tyr Glu Val Ser Pro Val Phe Leu Leu Val Glu Glu Ala Val Leu
145                 150                 155                 160

Lys Lys Met Ile Glu Phe Ile Gly Trp Lys Glu Gly Asp Gly Ile Phe
                165                 170                 175

Asn Pro Gly Gly Ser Val Ser Asn Met Tyr Ala Met Asn Leu Ala Arg
            180                 185                 190

Tyr Lys Tyr Cys Pro Asp Ile Lys Glu Lys Gly Leu Ser Gly Ser Pro
        195                 200                 205

Arg Leu Ile Leu Phe Thr Ser Ala Glu Cys His Tyr Ser Met Lys Lys
    210                 215                 220

Ala Ala Ser Phe Leu Gly Ile Gly Thr Glu Asn Val Cys Phe Val Glu
225                 230                 235                 240

Thr Asp Gly Arg Gly Lys Met Ile Pro Glu Glu Leu Glu Lys Gln Val
                245                 250                 255

Trp Gln Ala Arg Lys Glu Gly Ala Ala Pro Phe Leu Val Cys Ala Thr
            260                 265                 270

Ser Gly Thr Thr Val Leu Gly Ala Phe Asp Pro Leu Asp Glu Ile Ala
        275                 280                 285
```

```
Asp Ile Cys Glu Arg His Ser Leu Trp Leu His Val Asp Ala Ser Trp
    290                 295                 300

Gly Gly Ser Ala Leu Met Ser Arg Lys His Arg Lys Leu Leu His Gly
305                 310                 315                 320

Ile His Arg Ala Asp Ser Val Ala Trp Asn Pro His Lys Met Leu Met
            325                 330                 335

Ala Gly Ile Gln Cys Cys Ala Leu Leu Val Lys Asp Lys Ser Asp Leu
        340                 345                 350

Leu Lys Lys Cys Tyr Ser Ala Lys Ala Ser Tyr Leu Phe Gln Gln Asp
    355                 360                 365

Lys Phe Tyr Asp Val Ser Tyr Asp Thr Gly Asp Lys Ser Ile Gln Cys
370                 375                 380

Ser Arg Arg Pro Asp Ala Phe Lys Phe Trp Met Thr Trp Lys Ala Leu
385                 390                 395                 400

Gly Thr Leu Gly Leu Glu Arg Val Asn Arg Ala Leu Ala Leu Ser
            405                 410                 415

Arg Tyr Leu Val Asp Glu Ile Lys Lys Arg Glu Gly Phe Lys Leu Leu
                420                 425                 430

Met Glu Pro Glu Tyr Ala Asn Ile Cys Phe Trp Tyr Ile Pro Pro Ser
        435                 440                 445

Leu Arg Glu Met Glu Glu Gly Pro Glu Phe Trp Ala Lys Leu Asn Leu
    450                 455                 460

Val Ala Pro Ala Ile Lys Glu Arg Met Met Lys Lys Gly Ser Leu Met
465                 470                 475                 480

Leu Gly Tyr Gln Pro His Arg Gly Lys Val Asn Phe Phe Arg Gln Val
            485                 490                 495

Val Ile Ser Pro Gln Val Ser Arg Glu Asp Met Asp Phe Leu Leu Asp
        500                 505                 510

Glu Ile Asp Leu Leu Gly Lys Asp Met
    515                 520

<210> SEQ ID NO 2
<211> LENGTH: 3655
<212> TYPE: DNA
<213> ORGANISM: Homo sapiens
<220> FEATURE:
<221> NAME/KEY: misc_feature
<223> OTHER INFORMATION: GADL1

<400> SEQUENCE: 2
agactgcggg agccgcgccc ggggcagcct ggagtggggg agcggagatg agcagcgact      60
cggaccgcca gtgtcctgtg gacggagata ttgatcaaca agagatgatt ccaagtaaga     120
agaatgctgt tcttgtggat ggggttgtgc tgaatggtcc tacaacagat gcaaaagctg     180
gagaaaaatt tgttgaagag gcctgtaggc taataatgga agaggtggtt ttgaaagcta     240
cagatgtcaa tgagaaggtg tgtgaatgga ggcctcctga caactgaaa cagcttcttg     300 atttggagat gagagactca ggcgagccac cccataaact attggaactc tgtcgggatg     360
tcatacacta cagtgtcaaa actaaccacc caagattttt caaccaattg tatgctggac     420
ttgattatta ctccttggtg gcccgattta tgaccgaagc attgaatcca agtgtttata     480
cgtatgaggt gtccccagtg tttctgttag tggaagaagc ggttctgaag aaaatgattg     540
aatttattgg ctggaaagaa ggggatggaa tatttaaccc aggtggctca gtgtccaata     600
tgtatgcaat gaatttagct agatacaaat attgtcctga tattaaggaa aagggggctgt     660 ctggttcgcc aagattaatc cttttcacat ctgcagagtg tcattactct atgaagaagg     720
```

```
cagcctctttt tcttgggatt ggcactgaga atgtttgctt tgtggaaaca gatggaagag      780
gtaaaatgat acctgaggaa ctggagaagc aagtctggca agccagaaaa gagggggcag      840 caccgttttct tgtctgtgcc acttctggta caactgtgtt gggagctttt gaccctctgg     900
atgaaatagc agacatctgc gagaggcaca gcctctggct tcatgtagat gcttcttggg     960
gtggctcagc tttgatgtcg aggaagcacc gcaagcttct gcatggcatc cacagggctg    1020
actctgtggc ctggaaccca cacaagatgc tgatggctgg gatccagtgc tgtgctctcc    1080
ttgtgaaaga caaatctgat cttcttaaaa aatgctactc tgccaaggca tcttacctct    1140
tccagcagga taaattctat gatgtgagct atgacacagg agacaagtct atccagtgta    1200
gcagaagacc agatgcattc aagttctgga tgacctggaa ggccctgggt acattaggcc    1260
ttgaagaaag agttaatcgt gctcttgctt tatctaggta cctagtagat gaaatcaaga    1320
aaagagaagg attcaagtta ctgatggaac ctgaatatgc caatatttgc ttttggtaca    1380
ttccaccgag cctcagagag atggaagaag acccgagtt ctgggcaaaa cttaatttgg     1440
tggccccagc cattaaggag aggatgatga agaagggaag cttgatgctg ggctaccagc    1500
cgcaccgggg aaaggtcaac ttcttccgcc aggtggtgat cagccctcaa gtgagccggg    1560
aggacatgga cttcctcctg gatgagatag acttactggg taaagacatg tagctgtggc    1620
tttggtcccc cagaggcata gatcctatcc tgggagagtt tagatccaga acatcttgga    1680
gatacacagt agattgcagc ccttctgatg agaaatagg aatactccca gtccaggccc     1740
agcaaaacca aaatgctaag caatgaatat taaggactct ctagctgcct gggcattact    1800
gttgctaaaa gaagaaagtt taaaaaaaaa aatgatttc tcaaggaatg cccctggaac     1860
acagctctga agagagtta gtaagtacca tgtaggttct ggattctaag cttacattgc     1920
tctttaaaga acttataaac taacggttta aagcagtggt tctcaaagtg tggtccctgg    1980
actatcagca tcaaagcatc acctgggaac ttgctaaaaa tgcagattct caggcttttct   2040 ctagaccaac tggatcagaa gctctggggg tgaggcccag tattctgtgt tttaacaagc    2100
ccgtcaggga attctgatgc acagtaaaat ccgagaaaca ctggtttaag aaaaaccttg    2160
taatgatcga atacccactc tgatgttttg ccagcaaagg gatatctaat atttcagaag    2220
cctctgagcc agtctttgaa aaaatacaac tatggcatct gcagcacaaa tatttaagga    2280
catcagaagc atgtcaaagc tattttttaaa gagaaaact gtataagatg tttacttcat     2340
agagatttat gttttatgca ggctgaatgt ttatctcaaa agttaaaatt atccattctc     2400
aaaagttaaa attatatata tatatatata tacacacaca cacatatata tatatatata     2460
attcaaagca caataattga aagcacaata attgacagaa aaatacaggt tctattaata     2520
aattaataaa ctgttggtct tcaaaataga aatgcatgta atatccatat tagttttttc     2580
ttggtagaca actggaaggt tttcttttttt ttcgtctatg actaattttc tttattcaag    2640
atacctgaac tggggtgctt tttaagaaaa atttgggaaa tatatatgtt tctgtgatat     2700
acatatatac atatatatgt atatatatac acacacatac atatgtgtgt gtatagtata    2760
tatatatata cacacatata tgtttctgtg ttcctctttt agcttgaggg gcttgtttat     2820
tatcttgctc tgtgcctcat agggaataaa cacaatgaag tccagggttg tacaacattc    2880
cctttcctaa gctttgaaat gtcagtatag attattaagt ggtttatatt acagaatctg    2940
ggattcagca gactttcagt gtaaatgctt cctccatttc tcctgagagt gggtgatttt    3000
aattctatct ctgaccctgg tcctaggttt ctaggagagt tttgtttaac taagaaattg    3060
```

| | |
|---|---|
| acagaattca taggtgtggg tgtagagttc accaagataa gattatgaat ataattaaag | 3120 |
| gtctgcatta aaaggtgaat gattgaagag tgttaaagca ttagacttag cacattcaat | 3180 |
| aaccttttcg tactccattg ttaaccaatg tcatttaaat tttgagtact atttgctttt | 3240 |
| attgcttatt ttcattttag tgtgcacagt ttctcggtat ctctattggt caaagaatat | 3300 |
| taaatctgtc tctgaattac ttcaaattct caggtgaaac ctattggtgt gtgtgtgtgt | 3360 |
| gtgtgtgtgt ttattttgca tttcttgttg ccttttttgtt ttaatgtcta cataaaatat | 3420 |
| ttctaaaatt gatgtttgta acaatttggg tttcatgaaa caaaaaggaa cattactata | 3480 |
| cttagtgttg ttgactttc ttttcctgtc atctcctctt tactggattg taccaataca | 3540 |
| ttttagaagt gaactggact tggttggcat tttagtttaa tgactgaaaa agtaggttga | 3600 |
| aagctctctg tattttagtt aacaccttga ataaaatgga aaaagcagtt atagc | 3655 |

<210> SEQ ID NO 3
<211> LENGTH: 1566
<212> TYPE: DNA
<213> ORGANISM: Homo sapiens
<220> FEATURE:
<221> NAME/KEY: misc_feature
<223> OTHER INFORMATION: GADL1 coding region

<400> SEQUENCE: 3

| | |
|---|---|
| atgagcagcg actcggaccg ccagtgtcct gtggacggag atattgatca acaagagatg | 60 |
| attccaagta agaagaatgc tgttcttgtg gatggggttg tgctgaatgg tcctacaaca | 120 |
| gatgcaaaag ctggagaaaa atttgttgaa gaggcctgta ggctaataat ggaagaggtg | 180 |
| gttttgaaag ctacagatgt caatgagaag gtgtgtgaat ggaggcctcc tgaacaactg | 240 |
| aaacagcttc ttgatttgga gatgagagac tcaggcgagc cacccccataa actattggaa | 300 |
| ctctgtcggg atgtcataca ctacagtgtc aaaactaacc acccaagatt tttcaaccaa | 360 |
| ttgtatgctg gacttgatta ttactccttg gtgcccgat ttatgaccga agcattgaat | 420 |
| ccaagtgttt atacgtatga ggtgtcccca gtgtttctgt tagtggaaga gcggttctg | 480 |
| aagaaaatga ttgaatttat tggctggaaa gaagggggatg gaatatttaa cccaggtggc | 540 |
| tcagtgtcca atatgtatgc aatgaattta gctagataca aatattgtcc tgatattaag | 600 |
| gaaaaggggc tgtctggttc gccaagatta atccttttca catctgcaga gtgtcattac | 660 |
| tctatgaaga aggcagcctc ttttcttggg attggcactg agaatgtttg ctttgtggaa | 720 |
| acagatggaa gaggtaaaat gatacctgag gaactggaga agcaagtctg gcaagccaga | 780 |
| aaagaggggg cagcaccgtt tcttgtctgt gccacttctg gtacaactgt gttgggagct | 840 |
| tttgacccctc tggatgaaat agcagacatc tgcgagaggc acagcctctg gcttcatgta | 900 |
| gatgcttctt ggggtggctc agctttgatg tcgaggaagc accgcaagct tctgcatggc | 960 |
| atccacaggg ctgactctgt ggcctggaac ccacacaaga tgctgatggc tgggatccag | 1020 |
| tgctgtgctc tccttgtgaa agacaaatct gatcttctta aaaatgcta ctctgccaag | 1080 |
| gcatcttacc tcttccagca ggataaaatc tatgatgtga gctatgacac aggagacaag | 1140 |
| tctatccagt gtagcagaag accagatgca ttcaagttct ggatgacctg aaggccctg | 1200 |
| ggtacattag gccttgaaga aagagttaat cgtgctcttg ctttatctag gtacctagta | 1260 |
| gatgaaatca gaaaagaga aggattcaag ttactgatgg aacctgaata tgccaatatt | 1320 |
| tgcttttggt acattccacc gagcctcaga gagatgaag aaggaccga gttctgggca | 1380 |
| aaacttaatt tggtggcccc agccattaag gagaggatga tgaagaaggg aagcttgatg | 1440 |

-continued

```
ctgggctacc agccgcaccg gggaaaggtc aacttcttcc gccaggtggt gatcagccct    1500
caagtgagcc gggaggacat ggacttcctc ctggatgaga tagacttact gggtaaagac    1560
atgtag                                                                1566
```

```
<210> SEQ ID NO 4
<211> LENGTH: 476
<212> TYPE: PRT
<213> ORGANISM: Homo sapiens
<220> FEATURE:
<221> NAME/KEY: MISC_FEATURE
<223> OTHER INFORMATION: truncated GADL1

<400> SEQUENCE: 4
```

Met Ser Ser Asp Ser Asp Arg Gln Cys Pro Val Asp Gly Asp Ile Asp
1               5                   10                  15

Gln Gln Glu Met Ile Pro Ser Lys Lys Asn Ala Val Leu Val Asp Gly
            20                  25                  30

Val Val Leu Asn Gly Pro Thr Thr Asp Ala Lys Ala Gly Glu Lys Phe
        35                  40                  45

Val Glu Glu Ala Cys Arg Leu Ile Met Glu Glu Val Val Leu Lys Ala
    50                  55                  60

Thr Asp Val Asn Glu Lys Val Cys Glu Trp Arg Pro Pro Glu Gln Leu
65                  70                  75                  80

Lys Gln Leu Leu Asp Leu Glu Met Arg Asp Ser Gly Glu Pro Pro His
                85                  90                  95

Lys Leu Leu Glu Leu Cys Arg Asp Val Ile His Tyr Ser Val Lys Thr
            100                 105                 110

Asn His Pro Arg Phe Phe Asn Gln Leu Tyr Ala Gly Leu Asp Tyr Tyr
        115                 120                 125

Ser Leu Val Ala Arg Phe Met Thr Glu Ala Leu Asn Pro Ser Val Tyr
    130                 135                 140

Thr Tyr Glu Val Ser Pro Val Phe Leu Leu Val Glu Glu Ala Val Leu
145                 150                 155                 160

Lys Lys Met Ile Glu Phe Ile Gly Trp Lys Glu Gly Asp Gly Ile Phe
                165                 170                 175

Asn Pro Gly Gly Ser Val Ser Asn Met Tyr Ala Met Asn Leu Ala Arg
            180                 185                 190

Tyr Lys Tyr Cys Pro Asp Ile Lys Glu Lys Gly Leu Ser Gly Ser Pro
        195                 200                 205

Arg Leu Ile Leu Phe Thr Ser Ala Glu Gly Ala Ala Pro Phe Leu Val
    210                 215                 220

Cys Ala Thr Ser Gly Thr Thr Val Leu Gly Ala Phe Asp Pro Leu Asp
225                 230                 235                 240

Glu Ile Ala Asp Ile Cys Glu Arg His Ser Leu Trp Leu His Val Asp
                245                 250                 255

Ala Ser Trp Gly Gly Ser Ala Leu Met Ser Arg Lys His Arg Lys Leu
            260                 265                 270

Leu His Gly Ile His Arg Ala Asp Ser Val Ala Trp Asn Pro His Lys
        275                 280                 285

Met Leu Met Ala Gly Ile Gln Cys Cys Ala Leu Leu Val Lys Asp Lys
    290                 295                 300

Ser Asp Leu Leu Lys Lys Cys Tyr Ser Ala Lys Ala Ser Tyr Leu Phe
305                 310                 315                 320

Gln Gln Asp Lys Phe Tyr Asp Val Ser Tyr Asp Thr Gly Asp Lys Ser
                325                 330                 335

Ile Gln Cys Ser Arg Arg Pro Asp Ala Phe Lys Phe Trp Met Thr Trp
            340                 345                 350

Lys Ala Leu Gly Thr Leu Gly Leu Glu Glu Arg Val Asn Arg Ala Leu
            355                 360                 365

Ala Leu Ser Arg Tyr Leu Val Asp Glu Ile Lys Lys Arg Glu Gly Phe
        370                 375                 380

Lys Leu Leu Met Glu Pro Glu Tyr Ala Asn Ile Cys Phe Trp Tyr Ile
385                 390                 395                 400

Pro Pro Ser Leu Arg Glu Met Glu Gly Pro Glu Phe Trp Ala Lys
                405                 410                 415

Leu Asn Leu Val Ala Pro Ala Ile Lys Glu Arg Met Met Lys Lys Gly
            420                 425                 430

Ser Leu Met Leu Gly Tyr Gln Pro His Arg Gly Lys Val Asn Phe Phe
            435                 440                 445

Arg Gln Val Val Ile Ser Pro Gln Val Ser Arg Glu Asp Met Asp Phe
        450                 455                 460

Leu Leu Asp Glu Ile Asp Leu Leu Gly Lys Asp Met
465                 470                 475

<210> SEQ ID NO 5
<211> LENGTH: 1431
<212> TYPE: DNA
<213> ORGANISM: Homo sapiens
<220> FEATURE:
<221> NAME/KEY: misc_feature
<223> OTHER INFORMATION: truncated GADL1

<400> SEQUENCE: 5
atgagcagcg actcggaccg ccagtgtcct gtggacggag atattgatca acaagagatg      60
attccaagta agaagaatgc tgttcttgtg gatggggttg tgctgaatgg tcctacaaca     120
gatgcaaaag ctggagaaaa atttgttgaa gaggcctgta ggctaataat ggaagaggtg     180
gttttgaaag ctacagatgt caatgagaag gtgtgtgaat ggaggcctcc tgaacaactg     240
aaacagcttc ttgatttgga gatgagagac tcaggcgagc cacccccataa actattggaa     300 ctctgtcggg atgtcataca ctacagtgtc aaaactaacc acccaagatt tttcaaccaa     360
ttgtatgctg gacttgatta ttactccttg gtggcccgat ttatgaccga agcattgaat     420
ccaagtgttt atacgtatga ggtgtccccca gtgtttctgt tagtggaaga gcggttctg     480 aagaaaatga ttgaatttat tggctggaaa gaggggatg aatatttaa cccaggtggc     540 tcagtgtcca atatgtatgc aatgaattta gctagataca atattgtcc tgatattaag     600 gaaaagggc tgtctggttc gccaagatta tccttttca catctgcaga gggggcagca     660
ccgtttcttg tctgtgccac ttctggtaca actgtgttgg gagcttttga ccctctggat     720
gaaatagcag acatctgcga gaggcacagc ctctggcttc atgtagatgc ttcttgggt     780 ggctcagctt tgatgtcgag gaagcaccgc aagcttctgc atggcatcca cagggctgac     840
tctgtggcct ggaacccaca caagatgctg atggctggga tccagtgctg tgctctcctt     900
gtgaaagaca aatctgatct tcttaaaaaa tgctactctg ccaaggcatc ttacctcttc     960
cagcaggata aattctatga tgtgagctat gacacaggag acaagtctat ccagtgtagc    1020
agaagaccag atgcattcaa gttctggatg acctggaagg ccctgggtac attaggcctt    1080
gaagaaagag ttaatcgtgc tcttgcttta tctaggtacc tagtagatga aatcaagaaa    1140
agagaaggat tcaagttact gatggaacct gaatatgcca atatttgctt ttggtacatt    1200

```
ccaccgagcc tcagagagat ggaagaagga cccgagttct gggcaaaact taatttggtg    1260
gccccagcca ttaaggagag gatgatgaag aagggaagct tgatgctggg ctaccagccg    1320
caccggggaa aggtcaactt cttccgccag gtggtgatca gccctcaagt gagccgggag    1380
gacatggact tcctcctgga tgagatagac ttactgggta aagacatgta g             1431
```

GENETIC VARIANTS ASSOCIATED WITH LITHIUM RESPONSE IN BIPOLAR DISORDER

CROSS-REFERENCE TO RELATED APPLICATION

This is the U.S. national stage of International Application No. PCT/US2014/013561, filed on Jan. 29, 2014, which claims priority to US Provisional Application No. 61/757,855, filed on Jan. 29, 2013. The contents of both prior applications are thereby incorporated herein in their entirety.

BACKGROUND

Bipolar disorder is a disabling mental illness characterized by episodes of both elevated or irritable mood and depression. See, e.g., Müller-Oerlinghausen et al., Lancet 2002; 359:241-7; and Frye M A., N Engl J Med 2011; 364:51-9. Currently, lithium is the first-line choice for maintenance treatment in bipolar disorder and reduces risk of relapse and suicide. See, e.g., Fountoulakis et al., Eur Arch Psychiatry Clin Neurosci 2012; 262 Suppl 1:1-48. However, many patients do not respond to lithium treatment.

SUMMARY

Described herein is a method of determining lithium responsiveness in a bipolar disorder patient. The method includes: obtaining a sample from a patient having bipolar disorder; and assaying the sample for the presence or absence of one or more glutamate decarboxylase-like 1 (GADL1) gene variants selected from the group consisting of: (i) a T allele of the single nucleotide polymorphism (SNP) rs17026688; (ii) a G allele of the SNP rs17026651; (iii) GADL1 IVS8+48delG; (iv) a genetic variant that is associated or in linkage disequilibrium with SNP rs17026688, SNP rs17026651, or GADL1 IVS8+48delG, or a combination thereof; and (v) a haplotype containing or in linkage disequilibrium with SNP rs17026688, SNP rs17026651, or GADL1 IVS8+48delG, or a combination thereof. The presence of one or more of the GADL1 gene variants indicates that the patient is responsive to lithium treatment.

The sample can be a genomic DNA sample, RNA sample, cDNA sample, or protein sample obtained from a tissue or bodily fluid of the patient, e.g., blood or saliva. The assaying step can be performed by, for example, DNA sequencing, restriction enzyme digest, polymerase chain reaction (PCR), hybridization, real-time PCR, reverse transcriptase PCR, or ligase chain reaction, and an immunoassay. In one embodiment, the patient is a bipolar I disorder patient of Han Chinese descent.

Also described is a method of treating bipolar disorder in a patient. The method includes determining whether a patient carries one or more of the above-described GADL1 gene variants. If the patient carries one or more of the gene variants, the patient can be administered lithium treatment.

Further, described below is a kit for determining whether a subject carries one or more of the GADL1 gene variants described herein. The kit includes one or more probes for detecting the GADL1 variants.

The details of one or more embodiments are set forth in the description below. Other features, objects, and advantages of the embodiments will be apparent from the description and from the claims.

DETAILED DESCRIPTION

It was unexpected discover that certain variants of glutamate decarboxylase-like 1 (GADL1) are associated with lithium responsiveness in bipolar patients. A patient carrying one or more of these GADL1 variants is more likely to be responsive to lithium treatment.

GADL1 belongs to the group II decarboxylase family. The genomic location (chromosome 3), genomic DNA sequences (see, e.g., NC_000003.11 Reference GRCh37.p13 Primary Assembly, chr3:30767692-30936153), cDNA sequences (see, Accession No. NM_207359.2), and protein sequences of human GADL1 (see, e.g., Accession No. NP_997242.2) are known in the art.

The amino acid sequences of exemplary GADL1 polypeptides and cDNA sequences encoding the polypeptides are shown below.

```
Human GADL1 amino acid sequence
                                                            (SEQ ID NO: 1)
MSSDSDRQCPVDGDIDQQEMIPSKKNAVLVDGVVLNGPTTDAKAGEKFVEEACRLIMEEVVLKATDVN

EKVCEWRPPEQLKQLLDLEMRDSGEPPHKLLELCRDVIHYSVKTNHPRFFNQLYAGLDYYSLVARFMT

EALNPSVYTYEVSPVFLLVEEAVLKKMIEFIGWKEGDGIFNPGGSVSNMYAMNLARYKYCPDIKEKGL

SGSPRLILFTSAECHYSMKKAASFLGIGTENVCFVETDGRGKMIPEELEKQVWQARKEGAAPFLVCAT

SGTTVLGAFDPLDEIADICERHSLWLHVDASWGGSALMSRKHRKLLHGIHRADSVAWNPHKMLMAGIQ

CCALLVKDKSDLLKKCYSAKASYLFQQDKFYDVSYDTGDKSIQCSRRPDAFKFWMTWKALGILGLEER

VNRALALSRYLVDEIKKREGFKLLMEPEYANICFWYIPPSLREMEEGPEFWAKLNLVAPAIKERMMKK

GSLMLGYQPHRGKVNFFRQVVISPQVSREDMDFLLDEIDLLGKDM

Human GADL1 cDNA sequence
                                                            (SEQ ID NO: 2)
underlined - coding region
                                                            (SEQ ID NO: 3)
AGACTGCGGGAGCCGCGCCCGGGGCAGCCTGGAGTGGGGGAGCGGAGATGAGCAGCGACTCGGACCGCCAGTGTC

CTGTGGACGGAGATATTGATCAACAAGAGATGATTCCAAGTAAGAAGAATGCTGTTCTTGTGGATGGGGTTGTGC

TGAATGGTCCTACAACAGATGCAAAAGCTGGAGAAAAATTTGTTGAAGAGGCCTGTAGGCTAATAATGGAAGAGG
```

-continued

```
TGGTTTTGAAAGCTACAGATGTCAATGAGAAGGTGTGTGAATGGAGGCCTCCTGAACAACTGAAACAGCTTCTTG
ATTTGGAGATGAGAGACTCAGGCGAGCCACCCCATAAACTATTGGAACTCTGTCGGGATGTCATACACTACAGTG
TCAAAACTAACCACCCAAGATTTTTCAACCAATTGTATGCTGGACTTGATTATTACTCCTTGGTGGCCCGATTTA
TGACCGAAGCATTGAATCCAAGTGTTTATACGTATGAGGTGTCCCCAGTGTTTCTGTTAGTGGAAGAAGCGGTTC
TGAAGAAAATGATTGAATTTATTGGCTGGAAAGAAGGGGATGGAATATTTAACCCAGGTGGCTCAGTGTCCAATA
TGTATGCAATGAATTTAGCTAGATACAAATATTGTCCTGATATTAAGGAAAAGGGGCTGTCTGGTTCGCCAAGAT
TAATCCTTTTCACATCTGCAGAGTGTCATTACTCTATGAAGAAGGCAGCCTCTTTTCTTGGGATTGGCACTGAGA
ATGTTTGCTTTGTGGAAACAGATGGAAGAGGTAAAATGATACCTGAGGAACTGGAGAAGCAAGTCTGGCAAGCCA
GAAAAGAGGGGGCAGCACCGTTTCTTGTCTGTGCCACTTCTGGTACAACTGTGTTGGGAGCTTTTGACCCTCTGG
ATGAAATAGCAGACATCTGCGAGAGGCACAGCCTCTGGCTTCATGTAGATGCTTCTTGGGGTGGCTCAGCTTTGA
TGTCGAGGAAGCACCGCAAGCTTCTGCATGGCATCCACAGGGCTGACTCTGTGGCCTGGAACCCACACAAGATGC
TGATGGCTGGGATCCAGTGCTGTGCTCTCCTTGTGAAAGACAAATCTGATCTTCTTAAAAAATGCTACTCTGCCA
AGGCATCTTACCTCTTCCAGCAGGATAAATTCTATGATGTGAGCTATGACACAGGAGACAAGTCTATCCAGTGTA
GCAGAAGACCAGATGCATTCAAGTTCTGGATGACCTGGAAGGCCCTGGGTACATTAGGCCTTGAAGAAAGAGTTA
ATCGTGCTCTTGCTTTATCTAGGTACCTAGTAGATGAAATCAAGAAAAGAGAAGGATTCAAGTTACTGATGGAAC
CTGAATATGCCAATATTTGCTTTTGGTACATTCCACCGAGCCTCAGAGAGATGGAAGAAGGACCCGAGTTCTGGG
CAAAACTTAATTTGGTGGCCCCAGCCATTAAGGAGAGGATGATGAAGAAGGGAAGCTTGATGCTGGGCTACCAGC
CGCACCGGGGAAAGGTCAACTTCTTCCGCCAGGTGGTGATCAGCCCTCAAGTGAGCCGGGAGGACATGGACTTCC
TCCTGGATGAGATAGACTTACTGGGTAAAGACATGTAGCTGTGGCTTTGGTCCCCCAGAGGCATAGATCCTATCC
TGGGAGAGTTTAGATCCAGAACATCTTGGAGATACACAGTAGATTGCAGCCCTTCTGATGAGAAATAGGGAATAC
TCCCAGTCCAGGCCCAGCAAAACCAAAATGCTAAGCAATGAATATTAAGGACTCTCTAGCTGCCTGGGCATTACT
GTTGCTAAAAGAAGAAAGTTTAAAAAAAAAAATGATTTTCTCAAGGAATGCCCCTGGAACACAGCTCTGAAGAGA
GTTTAGTAAGTACCATGTAGGTTCTGGATTCTAAGCTTACATTGCTCTTTAAAGAACTTATAAACTAACGGTTTA
AAGCAGTGGTTCTCAAAGTGTGGTCCCTGGACTATCAGCATCAAAGCATCACCTGGGAACTTGCTAAAAATGCAG
ATTCTCAGGCTTTCTCTAGACCAACTGGATCAGAAGCTCTGGGGGTGAGGCCCAGTATTCTGTGTTTTAACAAGC
CCGTCAGGGAATTCTGATGCACAGTAAAATCCGAGAAACACTGGTTTAAGAAAAACCTTGTAATGATCGAATACC
CACTCTGATGTTTTGCCAGCAAAGGGATATCTAATATTTCAGAAGCCTCTGAGCCAGTCTTTGAAAAAATACAAC
TATGGCATCTGCAGCACAAATATTTAAGGACATCAGAAGCATGTCAAAGCTATTTTTAAAGAGAGAAACTGTATA
AGATGTTTACTTCATAGAGATTTATGTTTTATGCAGGCTGAATGTTTATCTCAAAAGTTAAAATTATCCATTCTC
AAAAGTTAAAATTATATATATATATATATACACACACACATATATATATATATATAATTCAAAGCACAATA
ATTGAAAGCACAATAATTGACAGAAAAATACAGGTTCTATTAATAAATTAATAAACTGTTGGTCTTCAAAATAGA
AATGCATGTAATATCCATATTAGTTTTTCTTGGTAGACAACTGGAAGGTTTTCTTTTTTTTCGTCTATGACTAA
TTTTCTTTATTCAAGATACCTGAACTGGGGTGCTTTTTAAGAAAAATTTGGGAAATATATATGTTTCTGTGATAT
ACATATATACATATATATGTATATATATACACACACATACATATGTGTGTATAGTATATATATATACACAC
ATATATGTTTCTGTGTTCCTCTTTTAGCTTGAGGGGCTTGTTTATTATCTTGCTCTGTGCCTCATAGGGAATAAA
CACAATGAAGTCCAGGGTTGTACAACATTCCCTTTCCTAAGCTTTGAAATGTCAGTATAGATTATTAAGTGGTTT
ATATTACAGAATCTGGGATTCAGCAGACTTTCAGTGTAAATGCTTCCTCCATTTCTCCTGAGAGTGGGTGATTTT
AATTCTATCTCTGACCCTGGTCCTAGGTTTCTAGGAGAGTTTTGTTTAACTAAGAAATTGACAGAATTCATAGGT
GTGGGTGTAGAGTTCACCAAGATAAGATTATGAATATAATTAAAGGTCTGCATTAAAAGGTGAATGATTGAAGAG
TGTTAAAGCATTAGACTTAGCACATTCAATAACCTTTTCGTACTCCATTGTTAACCAATGTCATTTAAATTTGA
GTACTATTTGCTTTTATTGCTTATTTTCATTTTAGTGTGCACAGTTTCTCGGTATCTCTATTGGTCAAAGAATAT
```

-continued

```
TAAATCTGTCTCTGAATTACTTCAAATTCTCAGGTGAAACCTATTGGTGTGTGTGTGTGTGTGTGTTTATT
TTGCATTTCTTGTTGCCTTTTTGTTTTAATGTCTACATAAAATATTTCTAAAATTGATGTTTGTAACAATTTGGG
TTTCATGAAACAAAAAGGAACATTACTATACTTAGTGTTGTTGACTTTTCTTTTCCTGTCATCTCCTCTTTACTG
GATTGTACCAATACATTTTAGAAGTGAACTGGACTTGGTTGGCATTTTAGTTTAATGACTGAAAAAGTAGGTTGA
AAGCTCTCTGTATTTTAGTTAACACCTTGAATAAAATGGAAAAAGCAGTTATAGC
```

A truncated human GADL1 isoform with exons 7 and 8 deleted
(SEQ ID NO: 4)
```
MSSDSDRQCPVDGDIDQQEMIPSKKNAVLVDGVVLNGPTTDAKAGEKFVEEACRLIMEEVVLKATDVN
EKVCEWRPPEQLKQLLDLEMRDSGEPPHKLLELCRDVIHYSVKTNHPRFFNQLYAGLDYYSLVARFMT
EALNPSVYTYEVSPVFLLVEEAVLKKMIEFIGWKEGDGIFNPGGSVSNMYAMNLARYKYCPDIKEKGL
SGSPRLILFTSAEGAAPFLVCATSGTTVLGAFDPLDEIADICERHSLWLHVDASWGGSALMSRKHRKL
LHGIHRADSVAWNPHKMLMAGIQCCALLVKDKSDLLKKCYSAKASYLFQQDKFYDVSYDTGDKSIQCS
RRPDAFKFWMTWKALGTLGLEERVNRALALSRYLVDEIKKREGFKLLMEPEYANICFWYIPPSLREME
EGPEFWAKLNLVAPAIKERMMKKGSLMLGYQPHRGKVNFFRQVVISPQVSREDMDFLLDEIDLLGKDM
``` cDNA sequence encoding SEQ ID NO:4
(SEQ ID NO: 5)
```
ATGAGCAGCGACTCGGACCGCCAGTGTCCTGTGGACGGAGATATTGATCAACAAGAGATGATTCCAAGTAAGAAG
AATGCTGTTCTTGTGGATGGGGTTGTGCTGAATGGTCCTACAACAGATGCAAAAGCTGGAGAAAAATTTGTTGAA
GAGGCCTGTAGGCTAATAATGGAAGAGGTGGTTTTGAAAGCTACAGATGTCAATGAGAAGGTGTGTGAATGGAGG
CCTCCTGAACAACTGAAACAGCTTCTTGATTTGGAGATGAGAGACTCAGGCGAGCCACCCCATAAACTATTGGAA
CTCTGTCGGGATGTCATACACTACAGTGTCAAAACTAACCACCCAAGATTTTTCAACCAATTGTATGCTGGACTT
GATTATTACTCCTTGGTGGCCCGATTTATGACCGAAGCATTGAATCCAAGTGTTTATACGTATGAGGTGTCCCCA
GTGTTTCTGTTAGTGGAAGAAGCGGTTCTGAAGAAAATGATTGAATTTATTGGCTGGAAAGAAGGGGATGGAATA
TTTAACCCAGGTGGCTCAGTGTCCAATATGTATGCAATGAATTTAGCTAGATACAAATATTGTCCTGATATTAAG
GAAAAGGGGCTGTCTGGTTCGCCAAGATTAATCCTTTTCACATCTGCAGAGGGGCAGCACCGTTTCTTGTCTGT
GCCACTTCTGGTACAACTGTGTTGGGAGCTTTTGACCCTCTGGATGAAATAGCAGACATCTGCGAGAGGCACAGC
CTCTGGCTTCATGTAGATGCTTCTTGGGGTGGCTCAGCTTTGATGTCGAGGAAGCACCGCAAGCTTCTGCATGGC
ATCCACAGGGCTGACTCTGTGGCCTGGAACCCACACAAGATGCTGATGGCTGGGATCCAGTGCTGTGCTCTCCTT
GTGAAAGACAAATCTGATCTTCTTAAAAAATGCTACTCTGCCAAGGCATCTTACCTCTTCCAGCAGGATAAATTC
TATGATGTGAGCTATGACACAGGAGACAAGTCTATCCAGTGTAGCAGAAGACCAGATGCATTCAAGTTCTGGATG
ACCTGGAAGGCCCTGGGTACATTAGGCCTTGAAGAAAGAGTTAATCGTGCTCTTGCTTTATCTAGGTACCTAGTA
GATGAAATCAAGAAAAGAGAAGGATTCAAGTTACTGATGGAACCTGAATATGCCAATATTTGCTTTTGGTACATT
CCACCGAGCCTCAGAGAGATGGAAGAAGGACCCGAGTTCTGGGCAAAACTTAATTTGGTGGCCCCAGCCATTAAG
GAGAGGATGATGAAGAAGGGAAGCTTGATGCTGGGCTACCAGCCGCACCGGGGAAAGGTCAACTTCTTCCGCCAG
GTGGTGATCAGCCCTCAAGTGAGCCGGGAGGACATGGACTTCCTCCTGGATGAGATAGACTTACTGGGTAAAGAC
ATGTAG
```

Two single nucleotide polymorphism (SNPs), rs17026688 and rs17026651, located in the introns of the GADL1 gene, and a 1-base deletion variant, IVS8+48delG, were found to be associated with lithium responsiveness. IVS8+48delG is a G deletion located in intron 8 of the GADL1 gene. Bipolar patients carrying the T allele of rs17026688, the G allele of rs17026651, and/or IVS8+48delG are more likely to respond to lithium treatment.

Described herein is a method of determining or predicting whether a bipolar patient is a good responder of lithium treatment. A bipolar patient (e.g., a bipolar I patient) can be identified using methods known in the art and described herein.

For example, the presence of the T allele of rs17026688 (e.g., genotype TT or CT) in a bipolar patient indicates that the patient is a good responder of lithium treatment. On the other hand, a patient carrying the C allele of rs17026688 (i.e., genotype CC) is less likely to have a good response to lithium. In another example, a bipolar patient carrying the G allele of rs17026651 (e.g., genotype GG or CG) is more likely to be a good responder of lithium treatment than a patient carrying the C allele (e.g., genotype CC). In yet another example, the presence of the IVS8+48delG variant in a bipolar patient indicates that the patient is a good lithium responder.

If a bipolar patient has one or more genetic variants associated with good lithium response, the patient can be administered lithium treatment. For a bipolar patient who lacks such variants, alternative therapeutics may be preferred. Alternative bipolar therapeutics include, but are not limited to, valproate, carbamazepine, oxcarbazepine, and lamotrigine.

Other GADL1 genetic markers may also be used to determine a bipolar patient's responsiveness to lithium. For examples, such genetic markers include known SNPs located in the GADL1 gene and those GADL1 variants described herein.

The presence of a genetic variant can be determined by direct detection of that variant or a particular region within it. Genomic DNAs for allele detection can be prepared from a patient by methods well known in the art. Detection of a region within a genetic marker of interest includes examining the nucleotide(s) located at either the sense or the anti-sense strand within that region. Methods known in the art can be used to detect a particular region or genetic variant, e.g., sequencing, sequence specific oligonucleotide-hybridization, real-time PCR, ligase chain reaction, or CSSO-ELISA (M. Hiratsuka et al, J. of Biochemical and Biophysic. Methods, 67:87-94, 2006).

The presence of an allele of interest also can be determined by detecting genetic markers equivalent to the allele. Genetic markers near the allele of interest tend to co-segregate, or show a linkage disequilibrium, with the allele. Consequently, the presence of these markers (equivalent genetic markers) is indicative of the presence of the allele of interest, which, in turn, is indicative of lithium responsiveness.

Alternatively or in addition, RNAs, cDNAs, or protein products of alleles of interest can be detected to determine the presence or absence of the alleles. For example, the IVS8+48delG variant results in a truncated form of GADL1 lacking exons 7 and 8. Mass spectrometry assays, e.g., MALDI-MS, LC-MS, and LC-MS/MS, and immunoassays, e.g., ELISA, Western blot, radioimmunoassay (RIA), fluorescent immunoassay (FIA), and luminescence immunoassay (LIA), can be used to determine the protein product of an allele. Reverse transcriptase PCR cab used to detect the mRNA product of an allele.

Genomic DNA, cDNA, RNA, or protein samples from patients can be prepared from various tissues and bodily fluids of the patients, e.g., blood, saliva, urine, and hair.

Also described herein is a kit containing probes for detecting one or more genetic markers, e.g., rs17026688, rs17026651, and IVS8+48delG. The term "probe" used herein refers to any substance useful for detecting another substance. Thus, a probe can be an oligonucleotide or conjugated oligonucleotide that specifically hybridizes to a particular region within an allele of interest. The conjugated oligonucleotide refers to an oligonucleotide covalently bound to chromophore or a molecules containing a ligand (e.g., an antigen), which is highly specific to a receptor molecular (e.g., an antibody specific to the antigen). The probe can also be a PCR primer, together with another primer, for amplifying a particular region within the allele of interest. Further, the probe can be an antibody that recognizes an allele of interest or a protein product of the allele. Optionally, the kit can contain a probe that targets an internal control allele, which can be any allele presented in the general population, e.g. GAPDH, β-actin, KIR. Detection of an internal control allele is designed to assure the performance of the kit. The probes can be immobilized on a solid support, e.g., an array.

The kit can further include tools and/or reagents for collecting biological samples from patients, as well as those for preparing genomic DNA, cDNAs, RNAs or proteins from the samples. For example, PCR primers for amplifying the relevant regions of the genomic DNA may be included.

In one example, the kit contains a first probe, a second probe, and a third probe, each for detecting the T allele of rs17026688, the G allele of rs17026651, or IVS8+48delG. These probes can each be a pair of PCR primers or a labeled oligonucleotide useful in hybridization assays. Optionally, the kit can include an additional probe for detecting an internal control allele.

The specific example below is to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are incorporated herein by reference in their entirety.

We selected subsets of participants from a sample of 1761 persons of Han Chinese descent with bipolar I (BPI) disorder recruited by the Taiwan Bipolar Consortium. We assessed response to lithium treatment using the Alda Scale, and carried out a genome-wide association study (GWAS) on 294 BPI patients receiving lithium treatment. The SNPs showing strongest association with response to lithium were then tested for association in a replication sample of 100 patients and further tested in a follow-up series of 24 patients. We sequenced the exons, exon-intron boundaries and part of the promoter of GADL1 in 94 responders and 94 non-responders from the GWAS sample.

We found that two SNPs in high linkage disequilibrium, rs17026688 and rs17026651, located in the introns of glutamate decarboxylase-like 1 (GADL1), showed the strongest associations in the GWAS (P=5.50×10$^{-37}$ and 2.52×10$^{-37}$) and the replication set of 100 patients (P=9.19×10$^{-15}$ for each SNP). These two SNPs had a sensitivity of 0.93 for predicting lithium response and differentiated between the good and poor responders in the follow-up cohort. Re-sequencing of GADL1 disclosed a novel variant, IVS8+48delG, which lies in intron 8 of the gene and is in complete linkage disequilibrium with rs17026688. IVS8+48delG was shown to affect splicing.

Our study showed that rs17026651, GADL1 IVS8+48delG, and rs17026688 are useful biomarkers in predicting response to lithium therapy in persons with BPI disorder. These alleles are rare in persons of European and African ancestry. Other variants in GADL1 may influence response to lithium therapy in these populations.

Methods

Participants

The study was conducted by Taiwan Bipolar Consortium established in 2003 with members from the Institute of Biomedical Sciences, Academia Sinica and 25 psychiatric departments of general hospitals and psychiatric institutions in Taiwan. The Consortium initially set out to understand genetic susceptibility to BPI disorder, and broadened its scope to the pharmacogenetic study of mood stabilizers. The first part of the study has been described previously. See, Lee et al., Mol Psychiatry 2011; 16:548-56. In brief, unrelated patients with BPI, aged 20 to 65, were recruited from the psychiatric departments and institutions of the Taiwan Bipolar Consortium. All of these patients had been diagnosed according to DSM-IV criteria for BPI disorder with recurrent episodes of mania with or without depressive episode(s). We excluded patients with other psychotic and affective disorders.

Psychiatric nurses and psychiatrists evaluated study participants using a cross-culturally validated Chinese version of the Schedules for Clinical Assessment in Neuropsychiatry (SCAN) (see, Cheng et al., Br J Psychiatry 2001; 178:567-72), supplemented by available medical records and reports from family members and in-charge psychiatrists. Only patients of Han-Chinese descent were considered for the study (ancestry was determined by verbal report of patients to members of the research team). We recruited 1761 BPI patients between March 2003 and the end of May 2012.

Study Design and Oversight

We carried out a "discovery" GWAS, and two tests of replication. For GWAS, we first identified 294 from 1647 (17.9%) persons with BPI consecutively recruited from outpatient clinics and inpatient units of the 25 psychiatric departments and institutions in the Taiwan Bipolar Consortium. We genotyped each of the 1647 patients by array (see below). The 294-patient GWAS sample had received lithium prophylaxis treatment with good adherence for at least two years. The remainder of the patients in the series did not. We identified genetic regions associated with response to lithium prophylaxis treatment, and then carried out a test of replication using SNPs marking these loci in an independent group of 100 persons with BPI disorder. These 100 patients were selected from 114 BPI patients (distinct from those in the sample of 1647 patients) referred to us by staff psychiatrists who had treated these patients for more than 10 years with lithium and observed good drug compliance. Fourteen of the 114 patients were excluded because they did not fulfil our inclusion criteria (see Phenotype Definition and Assessment below).

In a second test of replication, we genotyped an independent series of 24 patients who had received lithium monotherapy for at least 2 years, through May 2012. We based their inclusion on a life chart (see Phenotype Definition and Assessment below) constructed for all patients in the 1647-patient sample. Each of these 24 patients had good drug adherence to mood stabilizer(s) other than lithium prior to their commencement of lithium monotherapy but with unsatisfactory response.

The study was approved by the institutional review boards of participating hospitals and Academia Sinica, Taiwan, and we obtained written informed consent from all participants.

Phenotype Definition and Assessment

To assess response to long-term lithium prophylaxis treatment in BPI disorder, we prepared a life chart with graphic depiction of lifetime clinical course for each of the BPI patients recruited before June 2012 (N=1761). This life chart included all manic, hypomanic, and depressive episodes with date of onset (year and month), duration, and severity (including the extent of functional disability, hospitalization, and the presence of psychotic features), all doses of and duration of treatment with psychotropics and mood stabilizers known have been prescribed, drug adherence recorded in medical chart for all visits at outpatient clinics, all recorded blood levels of mood stabilizers, and any adverse drug reactions. We depicted this information graphically, based on integrated information gathered from direct interview with patients and their family members, interviews with in-charge psychiatrists, and a thorough medical chart review. Based on this life chart, we determined whether individual patients had good drug adherence.

The phenotype of lithium response was assessed based on the life chart, using the Retrospective Criteria of Long-Term Treatment Response in Research Subjects with Bipolar Disorder developed by Martin Alda and Colleagues (Alda Scale). The Alda scale has two criteria. Criterion A measures the extent of clinical improvement in illness activity and takes into account the frequency, duration, and severity of episodes during periods of lithium treatment considered adequate in duration and dosage, compared with the frequency, duration, and severity of episodes during periods off the lithium treatment, on a scale from 0 (no change, or exacerbation of disease severity) to 10 (complete remission). Criterion B (B1-B5, each rated as 0, 1 or 2 points) is used to establish whether there is a causal relationship between clinical improvement and the treatment. B1 and B2 indicate the recurrence risk off the lithium treatment [number (B1) and frequency (B2) of episodes]. B3 is a measure of the length of lithium treatment. B4 indicates compliance with lithium. B5 is a measure of concomitant psychotropic medication during periods of stability. The total score is obtained by subtracting the sum of the B scores from the A score.

In investigating a causal relationship between lithium treatment and clinical improvement of individual patients, it is important to ensure (i) comparability in clinical course between on-lithium and off-lithium periods (number, frequency and severity of episodes); (ii) satisfactory drug compliance, and (iii) the minimization of influence from additional medications (hypnotics, antidepressants, antipsychotics, and other mood stabilizers). We determined inclusion criteria accordingly, to minimize the misclassification of responders and non-responders. For example, we included patients showing poor response to lithium combined with prolonged use of antipsychotics or additional mood stabilizers, and excluded patients showing good response to lithium combined either with additional mood stabilizer throughout the course, or with prolonged use of high-dosage antipsychotics (B5=2). As shown in Table 1, nearly all of the study subjects (95.0%) with a B5 score of 2 were poor responders to treatment at the optimal cutoff of 5/6.

For patients in the second test of replication, we carried out regular follow-up evaluations (usually monthly and at least once every 3 months), including assay of lithium to assess drug adherence, and a SCAN interview to assess clinical condition, at outpatient clinics for at least 2 years.

An inter-rater reliability of the Alda Scale was carried out with 18 randomly selected BPI patients from the GWAS group. Three senior psychiatrists performed ratings based on the life chart. We observed an intraclass correlation among the 3 raters of 0.904 (see Table 2) for the total score (0-10).

TABLE 1

Distribution of additional medications in 394 bipolar I patients under lithium prophylaxis treatment

| Additional medications (B5) ¶ | N(%) |
|---|---|
| None except infrequent sleep medication (B5 = 0) ¶ | 47 (11.9) |
| Good response to treatment (A − B ≥ 6) ¶ | 30 (63.8) |
| Low dose antidepressants and/or antipsychotics and/or prolonged use of sleep medication (B5 = 1) ¶ | 246 (62.4) |
| Good response to treatment (A − B ≥ 6) ¶ | 124 (50.4) |
| Prolonged use of an antidepressant and/or antipsychotic and/or mood stabilizer (B5 = 2) ¶ | 101 (25.6) |
| Good response to treatment (A − B ≥ 6) ¶* | 5 (5.0) |
| Poor response to treatment (A − B < 6) ¶ | 96 (95.0) |
| Antidepressant only | 7 |
| Antipsychotic only | 40 |

TABLE 1-continued

Distribution of additional medications in 394 bipolar
I patients under lithium prophylaxis treatment

| Additional medications (B5) ¶ | N(%) |
|---|---|
| Antidepressant and antipsychotic | 3 |
| Carbamazepine with or without antidepressant/antipsychotic | 18 |
| Lamotrigine only | 2 |
| Valproate with or without antipsychotic | 21 |
| Both valproate and Carbamazepine, with or without antipsychotic | 5 |

¶ Scores measured by the Alda Scale, A – B represent total score weighted by factors that influence the degree to which the observed clinical change is considered to be due to lithium. In this study, the optimal cut-off point of A – B was found to be 5/6. *All with prolonged use of antidepressant.

TABLE 2

Interrater reliability of
the total Alda Scale
score among three raters.

| Study Subject | Raters | | |
|---|---|---|---|
| | A | B | C |
| 1 | 1 | 1 | 1 |
| 2 | 10 | 8 | 8 |
| 3 | 0 | 0 | 0 |
| 4 | 2 | 2 | 0 |
| 5 | 0 | 2 | 2 |
| 6 | 0 | 4 | 3 |
| 7 | 7 | 6 | 7 |
| 8 | 0 | 2 | 0 |
| 9 | 7 | 5 | 9 |
| 10 | 7 | 6 | 7 |
| 11 | 2 | −1 | 1 |
| 12 | 9 | 7 | 9 |
| 13 | 7 | 6 | 6 |
| 14 | 0 | 0 | 0 |
| 15 | 7 | 7 | 6 |
| 16 | 10 | 10 | 9 |
| 17 | 9 | 6 | 9 |
| 18 | 4 | 4 | 4 |

** Intraclass correlation among the 3 raters was estimated to be 0.904.

Outcomes

Previous studies using the Alda Scale have adopted a total score of 6/7 as the optimal cut-off point between non-responders (0-6) and responders (7-10) in lithium prophylaxis treatment. See, e.g., Grof et al., J Clin Psychiatry 2002; 63:942-7; and Squassina et al, Pharmacogenomics 2011; 12:1559-69. For the GWAS, we selected 4 potential cutoff points at 4/5, 5/6, 6/7 and 7/8 for classifying subjects with, respectively, greater than 50%, 65%, 80% and 90% reduction of illness activity as responders in lithium prophylaxis treatment.

Genotyping, Imputation, and Sequencing

We genotyped the 1647 participants using Illumina HumanHap550-Duo BeadChip and HumanOmni1-Quad BeadChip and integrated the two data sets through imputation with HapMap Phase 2 data. Quality control procedures were applied to the genotype data and the imputed data. We genotyped the top SNPs in the two replication series using SEQUENOM MassARRAY, and then sequenced GADL1 in 94 responders and 94 non-responders randomly selected from the GWAS group using Applied Biosystems 3730 DNA Sequencer.

Statistical Analysis

We compared the prevalence of alleles, implicated by GWAS, in non-responders and responders using the Cochran-Armitage trend test. The threshold P-value was set at $6.9 \times 10^{-9}$ after a Bonferroni corrected for the number of SNPs (1,814,186) and for the 4 different cut points. We examined P-value distributions using quantile-quantile (Q-Q) plots. We analyzed the GWAS data according to the 4 cutoff points to classify non-responders and responders. We also evaluated the top hits with adjustments for psychotic features (delusion and hallucination), family history of BPI in first-degree relatives, rapid cycling, age at onset, sex, and history of alcoholism using PLINK v. 1.07.

Results

The Study Participants

Demographic and clinical characteristics of the 394 study participants of the GWAS and Replication set are shown in Table 3, which includes clinical phenotypes previously reported to be associated with lithium responses. The median age was 49 years old and males and females were similar in proportion. A high proportion of study subjects were found to have a history of psychotic features (60%). The percentages of rapid cycling and family history of BPI in the first-degree relatives were 25% and 31%, respectively. Early-onset disease occurred in 15% and a history of alcoholism in 8% of the study participants.

TABLE 3

Demographic and Clinical Characteristics
of Study Persons (N = 394).

| Characteristics | N (%) |
|---|---|
| Median age at study entry-yr (range) | 49 (23-80) |
| Male sex-no. (%) | 191 (48.5) |
| Family history of BPI disorder in first-degree relatives-no. (%)¶ | 121 (30.7) |
| Early onset (≤15 yr)-no. (%) | 60 (15.2) |
| History of alcoholism-no. (%) | 31 (7.9) |
| Presence of psychotic features-no. (%)* | 238 (60.4) |
| Presence of rapid cycling-no. (%)† | 97 (24.6) |
| No. of episodes off lithium treatment (B1)-median no. (range)‡ | 6 (4-144) |
| Frequency of episodes off lithium treatment per year (B2)-median no. (range)‡ | 1 (0.4-15) |
| Duration of lithium treatment (B3)-median yr (range)‡ | 7 (2-28) |
| Excellent compliance to lithium treatment (B4)-no. (%)‡ | 394 (100) |
| Additional medication during the period of stability (B5)-no. (%)‡ | 347 (88.1) |
| None except infrequent sleep medication | 48 (12.2) |
| Low dose antidepressants and/or antipsychotics and/or prolonged use of sleep medication-no. (%) | 246 (62.4) |
| Prolonged use of an antidepressant and/or antipsychotic and/or mood stabilizer-no. (%) | 101 (25.6) |

BPI: bipolar 1
¶Include parents, children, and sibs.
*Include mood-incongruent delusions and hallucinations during manic and depressive episodes.
†At least four episodes of manic, depressive, or hypomanic episodes in the previous 12 months.
‡B1-B5 in Alda Scale. All the study patients had a rating of 0 for B1-B4 according to the criteria. They all had at least 4 episodes of mood disturbance (B1 = 0) and average frequency of episodes ≥0.5 per year (B2 = 0); had received lithium treatment for at least 2 years (B3 = 0), and had excellent drug compliance during periods(s) of stability (B4 = 0).

During off-lithium periods, the median number of episodes was 6 with a range of 4 to 144 and the median frequency of episodes was 1 per year with 0.4 (1 per 2.5 years) as the lowest. The median duration of lithium prophylaxis therapy with good adherence among study patients was 7 years, the shortest being 2 years. The reported lithium blood levels were equal to or exceeded 0.5 mM. We compared disease activity during periods with good adherence to activity during off-lithium periods. We observed that a high proportion of participants (88%) were found to be taking other drugs, and a quarter of them had received a prolonged course of antidepressant, antipsychotic, and/or mood stabilizer, in addition to lithium. See Table 4 for the distribution of the Alda Scale scores in the GWAS and replication groups.

TABLE 4

Frequency distributions of the total score of Alda Scale in the GWAS and replication groups.

| A-B | GWAS Group (N = 294) | Replication Group (N = 100) |
|---|---|---|
| 0 | 95 (32.3%) | 11 (11.0%) |
| 1 | 19 (6.5%) | 6 (6.0%) |
| 2 | 14 (4.8%) | 6 (6.0%) |
| 3 | 26 (8.8%) | 4 (4.0%) |
| 4 | 16 (5.4%) | 15 (15.0%) |
| 5 | 15 (5.1%) | 8 (8.0%) |
| 6 | 28 (9.5%) | 11 (11.0%) |
| 7 | 18 (6.1%) | 8 (8.0%) |
| 8 | 23 (7.8%) | 14 (14.0%) |
| 9 | 33 (11.2%) | 13 (13.0%) |
| 10 | 7 (2.4%) | 4 (4.0%) |

Association Analysis

We did not observe substantial population stratification nor cryptic genetic relationships among the 294 subjects analyzed by GWAS. SNPs on chromosome 3p24.1 showed association with response to lithium at genome-wide significance ($P<6.9\times10^{-9}$); no other chromosome region showed an association with genome-wide significance (Summary statistics from the genomewide association study can be found in the database of Genotypes and Phenotypes [dbGaP] of the National Center for Biotechnology Information, accession number phs000692.v1.p1.). Two SNPs in particular, rs17026688 and rs17026651, located in the introns of GADL1, encoding glutamate decarboxylase-like 1, approximately 7.2 kilobases apart, showed the strongest associations, with a cutoff point of 5/6 ($P=5.50\times10^{-37}$ and $2.52\times10^{-37}$, respectively). The highest sensitivity and specificity for response to lithium were 0.93 and 0.85 for rs17026688, and 0.93 and 0.86 for rs17026651 at this cutoff point (Table 5).

TABLE 5

Odd ratio, sensitivity, and specificity of rs17026688 and rs17026651 at different cut-off points for the total scores of Alda Scale.

| N = 294 | Cut-off* | OR (95% CI) | Sensitivity (95% CI) | Specificity (95% CI) |
|---|---|---|---|---|
| RS17026688 | 4/5 | 39.6 (19.3, 82.2) | 0.855 (0.780, 0.912) | 0.871 (0.811, 0.917) |
|  | 5/6 | 73.9 (30.8, 191) | 0.927 (0.860, 0.968) | 0.854 (0.795, 0.902) |
|  | 6/7 | 31.1 (13.1, 83.9) | 0.914 (0.830, 0.965) | 0.746 (0.683, 0.803) |
|  | 7/8 | 21.4 (8.6, 62.9) | 0.905 (0.804, 0.964) | 0.693 (0.629, 0.751) |
| Rs17026651 | 4/5 | 41.8 (20.2, 87.3) | 0.855 (0.780, 0.912) | 0.876 (0.817, 0.922) |
|  | 5/6 | 77.2 (32.1, 200.) | 0.927 (0.860, 0.968) | 0.859 (0.801, 0.906) |
|  | 6/7 | 31.9 (13.4, 86.0) | 0.914 (0.830, 0.965) | 0.751 (0.688, 0.808) |
|  | 7/8 | 21.9 (8.8, 64.2) | 0.905 (0.804, 0.964) | 0.697 (0.633, 0.756) |

TABLE 5-continued

Odd ratio, sensitivity, and specificity of rs17026688 and rs17026651 at different cut-off points for the total scores of Alda Scale.

| N = 394 | Cut-off* | OR (95% CI) | Sensitivity (95% CI) | Specificity (95% CI) |
|---|---|---|---|---|
| RS17026688 | 4/5 | 41.1 (22.2, 76.7) | 0.846 (0.785, 0.895) | 0.882 (0.830, 0.922) |
|  | 5/6 | 88.5 (41.4, 198) | 0.930 (0.879, 0.964) | 0.868 (0.818, 0.908) |
|  | 6/7 | 32.7 (15.8, 73.3) | 0.916 (0.852, 0.959) | 0.748 (0.692, 0.798) |
|  | 7/8 | 20.7 (9.8, 48.5) | 0.904 (0.826, 0.955) | 0.686 (0.630, 0.738) |
| Rs17026651 | 4/5 | 43.0 (23.1, 80.8) | 0.846 (0.785, 0.895) | 0.886 (0.836, 0.926) |
|  | 5/6 | 91.9 (42.8, 206) | 0.930 (0.879, 0.964) | 0.872 (0.822, 0.912) |
|  | 6/7 | 33.3 (16.0, 74.7) | 0.916 (0.852, 0.959) | 0.751 (0.696, 0.801) |
|  | 7/8 | 21.0 (9.9, 49.2) | 0.904 (0.826, 0.955) | 0.690 (0.634, 0.741) |

*According to the total scores of Alda Scale in 294 bipolar 1 patients.

We then genotyped rs17026688 and rs17026651, together with flanking SNPs that showed genomewide significance in the GWAS, in GADL1 in the replication group. Both rs17026688 and rs17026651 showed the strongest associations in the test of replication ($P=9.19\times10^{-15}$ for both SNPs). The distributions of allele prevalence were not significantly different for the top SNPs in the GWAS and replication samples. The P values of rs17026688 and rs17026651 in the combined series, comprising 394 study participants, were $P=1.66\times10^{-49}$ and $7.07\times10^{-50}$, respectively (Table 6).

Fisher's exact test for association between allele status and good responder status in the combined series yielded P values of $6.69\times10^{-62}$ and $8.30\times10^{-63}$, respectively (Table 7). We observed the two SNPs to be in high or absolute linkage disequilibrium (In the GWAS, D'=1.0 and $r^2$=96.6%, and in the replication group, D'=1.0 and $r^2$=100%).

TABLE 6

A genome-wide association study of response to lithium prophylaxis treatment among bipolar 1 patients: Cochran-Armitage trend test of 29 significant SNPs*

| SNP | Chromosome | Physical Position† | GWAS[1] (N = 294) P Value | Replication[2] (N = 100) P Value | Joint analysis[3] (N = 394) P Value |
|---|---|---|---|---|---|
| rs1158454 | 3 | 30830280 | 8.56E−16 | 2.18E−10 | 3.48E−24 |
| rs1910333 | 3 | 30832232 | 1.64E−08 | 4.09E−03 | 1.78E−10 |
| rs17026628 | 3 | 30832324 | 1.18E−23 | 4.66E−10 | 2.89E−32 |
| rs869484 | 3 | 30838465 | 1.18E−08 | 1.04E−03 | 3.15E−11 |
| rs17026642 | 3 | 30844064 | 2.76E−24 | 1.42E−11 | 6.88E−34 |
| rs17026643 | 3 | 30845750 | 5.11E−09 | 7.06E−04 | 1.50E−11 |
| rs1494730 | 3 | 30846244 | 4.01E−10 | 1.24E−03 | 1.46E−12 |
| rs6780262 | 3 | 30846680 | 3.26E−09 | 6.77E−04 | 9.80E−12 |
| rs1494731 | 3 | 30846903 | 3.26E−09 | 1.24E−03 | 1.50E−11 |
| rs6771562 | 3 | 30846936 | 6.91E−18 | 1.73E−11 | 1.15E−26 |
| rs1494732 | 3 | 30847081 | 3.26E−09 | 1.24E−03 | 1.50E−11 |
| rs13318432 | 3 | 30848144 | 1.79E−08 | 1.04E−03 | 4.90E−11 |
| rs2220850 | 3 | 30848648 | 6.91E−18 | 1.73E−11 | 1.15E−26 |
| rs1353275 | 3 | 30848764 | 2.70E−09 | 7.27E−04 | 7.65E−12 |
| rs1389908 | 3 | 30853295 | 8.76E−12 | 8.21E−04 | 5.82E−14 |
| rs17026651‡ | 3 | 30854362 | 2.52E−37 | 9.19E−15 | 7.07E−50 |
| rs931557 | 3 | 30854776 | 6.98E−12 | 5.58E−04 | 1.26E−14 |
| rs11709194 | 3 | 30859293 | 7.10E−15 | 6.23E−09 | 1.38E−21 |
| rs17026688‡ | 3 | 30861821 | 5.50E−37 | 9.19E−15 | 1.66E−49 |
| rs6792186 | 3 | 30867723 | 5.49E−11 | 2.92E−02 | 2.22E−11 |
| rs7652680 | 3 | 30872827 | 2.60E−08 | 1.88E−01 | 6.62E−08 |

TABLE 6-continued

A genome-wide association study of response to lithium
prophylaxis treatment among bipolar 1 patients:
Cochran-Armitage trend test of 29 significant SNPs*

| SNP | Chromosome | Physical Position† | GWAS[1] (N = 294) P Value | Replication[2] (N = 100) P Value | Joint analysis[3] (N = 394) P Value |
|---|---|---|---|---|---|
| rs6775621 | 3 | 30878650 | 1.66E−11 | 5.26E−03 | 8.17E−13 |
| rs4955342 | 3 | 30878747 | 8.67E−12 | 5.26E−03 | 4.94E−13 |
| rs4955346 | 3 | 30879119 | 1.76E−10 | 6.90E−02 | 2.95E−10 |
| rs4521277 | 3 | 30879801 | 3.66E−10 | 6.90E−02 | 5.29E−10 |
| rs4955348 | 3 | 30879848 | 2.14E−09 | 3.08E−02 | 7.58E−10 |
| rs1389903 | 3 | 30880388 | 3.66E−10 | 6.90E−02 | 5.29E−10 |
| rs7641301 | 3 | 30881421 | 3.08E−09 | 3.85E−02 | 1.20E−09 |
| rs9842693 | 3 | 30885556 | 1.63E−08 | 3.08E−02 | 4.54E−09 |

*Non-responders: total scores in Alda Scale 0-5; Respondents: total score in Alda Scale 6-10.
†The Physical positions were annotated according to NCBI build 36.
‡The results of rs17026651 and rs17026688 were based on re-sequencing data using ABI 3730 sequencers.
Data used for all other SNPs were described below:
[1]The results were based on the imputed GWAS genotype data and confirmed by Sequenom MassARRAY ® iPLEX Gold (consistent rate >95%)
[2]The results were based on the genotyped data using Sequenom MassARRAY ® iPLEX Gold.
[3]The results were based on the combined data of the above two data sets.

Among the 24 patients in the second test of replication (the follow-up study), the two top SNPs were also in complete linkage disequilibrium. All carriers of the "response" alleles (N=16) showed good response to lithium treatment (total Alda score ranged 8-10), and all of the non-carriers (N=8) showed poor response (total Alda score ranged 0-3) (Table 8). The GWAS (N=394) and the follow-up (N=24) study reached an acceptable power of 0.85 and 0.95, respectively.

TABLE 8

Results of follow up among 24 bipolar 1 patients in response to lithium prophylaxis treatment.

| Study Subject | Genotype of rs17026688 | Duration of follow-up (yrs) | A − B† | B5‡ |
|---|---|---|---|---|
| 1 | TT | 3 | 9 | 0 |
| 2 | TT | 3 | 9 | 0 |
| 3 | TT | 3.2 | 9 | 1 |
| 4 | TT | 5 | 9 | 1 |
| 5 | CT | 3 | 10 | 0 |
| 6 | CT | 2.8 | 10 | 0 |
| 7 | CT | 2 | 10 | 0 |
| 8 | CT | 3 | 10 | 1 |
| 9 | CT | 3 | 10 | 1 |

TABLE 7

P values of $\chi^2$ test and Fisher's exact test for the associations between the effective allele carriers and responders* (N = 394).

| SNP | Chromosome | Position† | Effective allele | $\chi^2$ test P Value | Fisher's exact test P Value | Odds ratio (95% CI) |
|---|---|---|---|---|---|---|
| rs1158454 | 3 | 30830280 | C | 2.03E−20 | 1.67E−22 | 12.98 (6.83, 26.25) |
| rs1910333 | 3 | 30832232 | G | 4.84E−06 | 1.30E−06 | 8.19 (2.86, 32.03) |
| rs17026628 | 3 | 30832324 | G | 3.31E−30 | 1.03E−31 | 14.95 (8.77, 25.73) |
| rs869484 | 3 | 30838465 | T | 3.98E−05 | 2.07E−05 | 8.50 (2.58, 43.91) |
| rs17026642 | 3 | 30844064 | G | 4.94E−33 | 7.49E−35 | 17.64 (10.22, 30.71) |
| rs17026643 | 3 | 30845750 | G | 4.03E−07 | 6.46E−08 | 9.68 (3.41, 37.64) |
| rs1494730 | 3 | 30846244 | C | 7.00E−08 | 5.96E−09 | 10.74 (3.80, 41.65) |
| rs6780262 | 3 | 30846680 | C | 1.08E−07 | 1.07E−08 | 10.47 (3.70, 40.64) |
| rs1494731 | 3 | 30846903 | T | 2.56E−07 | 3.51E−08 | 9.95 (3.51, 38.66) |
| rs6771562 | 3 | 30846936 | C | 2.22E−25 | 5.50E−27 | 12.98 (7.43, 23.19) |
| rs1494732 | 3 | 30847081 | A | 2.56E−07 | 3.51E−08 | 9.95 (3.51, 38.66) |
| rs13318432 | 3 | 30848144 | A | 3.98E−05 | 2.07E−05 | 8.50 (2.58, 43.91) |
| rs2220850 | 3 | 30848648 | G | 2.22E−25 | 5.50E−27 | 12.98 (7.43, 23.19) |
| rs1353275 | 3 | 30848764 | T | 1.67E−07 | 1.93E−08 | 10.21 (3.61, 39.65) |
| rs1389908 | 3 | 30853295 | A | 2.72E−10 | 2.16E−10 | 4.18 (2.59, 6.81) |
| rs17026651‡ | 3 | 30854362 | G | 1.17E−55 | 8.30E−63 | 91.94 (42.83, 206.55) |
| rs931557 | 3 | 30854776 | A | 7.23E−08 | 2.30E−09 | 34.38 (5.68, 1398) |
| rs11709194 | 3 | 30859293 | C | 1.88E−19 | 4.66E−22 | 17.19 (7.96, 42.13) |
| rs17026688‡ | 3 | 30861821 | T | 4.90E−55 | 6.69E−62 | 88.54 (41.40, 198.41) |
| rs6792186 | 3 | 30867723 | T | 1.70E−08 | 3.97E−09 | 6.65 (3.15, 15.63) |
| rs7652680 | 3 | 30872827 | A | 6.56E−04 | 4.77E−04 | 8.52 (2.05, 75.32) |
| rs6775621 | 3 | 30878650 | A | 1.02E−10 | 7.26E−12 | 8.28 (3.94, 19.38) |
| rs4955342 | 3 | 30878747 | G | 1.02E−10 | 7.26E−12 | 8.28 (3.94, 19.38) |
| rs4955346 | 3 | 30879119 | G | 2.17E−06 | 2.22E−07 | 26.73 (4.36, 1093) |
| rs4521277 | 3 | 30879801 | G | 2.17E−06 | 2.22E−07 | 26.73 (4.36, 1093) |
| rs4955348 | 3 | 30879848 | T | 4.98E−06 | 4.51E−07 | 24.91 (4.05, 1020) |
| rs1389903 | 3 | 30880388 | C | 2.17E−06 | 2.22E−07 | 26.73 (4.36, 1093) |
| rs7641301 | 3 | 30881421 | G | 4.81E−06 | 4.38E−07 | 25.00 (4.06, 1024) |
| rs9842693 | 3 | 30885556 | A | 3.11E−06 | 4.34E−07 | 25.94 (4.22, 1061) |

*Total score of Alda Scale ≥ 6.
†The physical positions were annotated according to NCBI build 36.
‡The results of rs17026688 and rs17026651 were based on re-sequencing data using ABI 3730 sequencers.
Data used for all other SNPs were based on the combined data of two data sets: the imputed GWAS genotype data (N = 294), which were confirmed by Sequenom MassARRAY ® iPLEX Gold (consistent rate > 95%) and the replication data (N = 100), which were genotyped using Sequenom MassARRAY ® iPLEX Gold.

TABLE 8-continued

Results of follow up among 24 bipolar 1 patients in response to lithium prophylaxis treatment.

| Study Subject | Genotype of rs17026688 | Duration of follow-up (yrs) | A – B[†] | B5[‡] |
|---|---|---|---|---|
| 10 | CT | 3 | 9 | 1 |
| 11 | CT | 3.5 | 9 | 1 |
| 12 | CT | 4.6 | 9 | 1 |
| 13 | CT | 2 | 9 | 1 |
| 14 | CT | 4.2 | 9 | 1 |
| 15 | CT | 3.6 | 9 | 1 |
| 16 | CT | 5 | 8 | 1 |
| 17 | CC | 2.2 | 3 | 0 |
| 18 | CC | 2 | 3 | 1 |
| 19 | CC | 3.6 | 3 | 1 |
| 20 | CC | 4 | 2 | 1 |
| 21 | CC | 4 | 2 | 2 |
| 22 | CC | 2 | 0 | 2 |
| 23 | CC | 3.3 | 0 | 2 |
| 24 | CC | 4.2 | 0 | 2 |

[†]Total score of Alda Scale
[‡]In Alda Scale, assessing additional medication during the period of stability with lithium treatment:
0 = None except infrequent sleep medication (one dose per week or less)
1 = Low dose antidepressants and/or antipsychotics and/or prolonged use of sleep medication
2 = Prolonged use of an antidepressant and/or antipsychotic and/or mood stabilizer We carried out further analyses of rs17026688 (Table 9). To assess the influence of other factors that might contribute to lithium response, we performed logistic regression analyses on data from all 394 participants (Table 10). We found that the "response" allele T at rs17026688 was associated with a much better response to lithium than was the alternative allele ($P=3.39 \times 10^{-32}$, OR=111.87, 95% CI 51.14-244.73, PPV=0.83, 95% CI 0.76, 0.88). In addition, patients with rapid cycling (irrespective of genetic status) had slightly better lithium response than those without ($P=8.47 \times 10^{-4}$, OR=3.88, 95% CI 1.75-8.59). Under the same logistic regression model, the other 21 flanking SNPs showed nominal significance or non-significance when conditioned on rs17026688 (all P values>0.00185, Table 11).

Re-Sequencing GADL1

Because the SNPs showing strongest association are in the introns of GADL1, we next looked for local variants likely to affect the expression of GADL1. Ninety-four responders and 94 non-responders were randomly selected from the 294-person GWAS set for sequence analysis of the exons, intron-exon boundaries, and a 2-kb region representing part of the promoter of GADL1. We found 32 genetic polymorphisms (Table 12), including a 1-base deletion in intron 8 of GADL1 (GADL1 IVS8+48delG). We genotyped this variant in the all participants of each of the three parts of our study (N=417) and found it to be in complete linkage disequilibrium with rs17026688.

Effect of the IVS8+48delG Variant

To test the effect of IVS8+48delG variant on splicing of GADL1 mRNA, we determined the mRNA isoforms via RT-PCR in two glioma-derived neural cell lines. One line (GBM S1R1) carries a IVS8+48delG variant and the other (GBM8401) carries two non-mutant alleles. We detected two GADL1 mRNA isoforms: GBM8401 expressed the major mRNA isoform (499 bp) containing exons 5 to 10. We also detected the minor splice variant (364 bp) containing exons 5, 6, 9 and 10 (exons 7 and 8 were omitted, presumably by alternative splicing). Compared with the cell line GBM8401, the cell line GBM S1R1 (which carried the IVS8+48delG variant), showed low levels of the major isoform and elevated levels of the smaller alternatively-spliced mRNA species.

TABLE 9

The Allele Prevalence of rs17026688 in Lithium Responders[†] and Non-responders[‡]

| | Genotype of rs17026688 | GWAS* (N = 294) | Replication (N = 100) | Combined (N = 394) |
|---|---|---|---|---|
| Responder (6-10) | TT | 31 | 6 | 37 |
| | CT | 70 | 41 | 111 |
| | CC | 8 | 3 | 11 |
| | Total | 109 | 50 | 159 |
| Non-responders (0-5) | TT | 2 | 1 | 3 |
| | CT | 25 | 3 | 28 |
| | CC | 158 | 46 | 204 |
| | Total | 185 | 50 | 235 |
| Trend test P values | | $5.50 \times 10^{-37}$ | $9.19 \times 10^{-15}$ | $1.66 \times 10^{-49}$ |
| Responder (6-10) | TT + CT | 101 | 47 | 148 |
| | CC | 8 | 3 | 11 |
| | Total | 109 | 50 | 159 |
| Non-responders (0-5) | TT + CT | 27 | 4 | 31 |
| | CC | 158 | 46 | 204 |
| | Total | 185 | 50 | 235 |
| Fisher exact test P-value | | $6.18 \times 10^{-43}$ | $9.17 \times 10^{-20}$ | $6.69 \times 10^{-62}$ |
| Odds ratio (95% CI) | | 73.9 (30.8, 191) | 180 (32.7, 1173) | 82.2 (36.2, 195.6) |
| Sensitivity % (95% CI) | | 92.7 (86.0, 96.8) | 94.0 (83.4, 98.7) | 93.0 (87.9, 96.4) |
| Specificity % (95% CI) | | 85.4 (79.5, 90.2) | 92.0 (80.7, 97.7) | 86.8 (81.8, 90.8) |
| Positive predictive value % (95% CI) | | 78.9 (70.8, 85.6) | 92.1 (81.1, 97.8) | 82.6 (76.3, 87.9) |
| Negative predictive value % (95% CI) | | 95.1 (90.7, 97.9) | 93.8 (83.1, 98.7) | 94.8 (91.0, 97.4) |
| Accuracy % (95% CI) | | 88.1 (83.8, 91.5) | 93.0 (86.1, 97.1) | 89.3 (85.8, 92.2) |

*Genome-wide association study
[†]Total Alda score = 6-10
[‡]Total Alda score = 0-5

TABLE 10

Genetic and clinical factors contributing to response to lithium prophylaxis treatment among bipolar 1 patients (N = 394): Logistic regression model*

| Variable | Odds Ratio | P Value |
|---|---|---|
| rs17026688 | 111.87 (51.14-244.73) | $3.39 \times 10^{-32}$ |
| Family history | 1.24 (0.6-2.56) | 0.562 |
| Early onset | 1.53 (0.6-3.9) | 0.368 |
| Alcoholism | 1.96 (0.58-6.7) | 0.281 |
| Psychosis | 0.86 (0.43-1.72) | 0.660 |
| Rapid cycling | 3.88 (1.75-8.59) | $8.47 \times 10^{-4}$ |
| Gender | 1.23 (0.61-2.48) | 0.563 |

*Logit (responder) = rs17026688 + Family history + Early onset + Alcoholism + Psychosis + Rapid cycling + Gender, where the variables were coded as 1 for the following definition and 0 for others:
Responders with a total score in Alda Scale from 6 to 10
Rs17026688: the carriers of effective allele T
Family history: BPI in first-degree relatives (parents, children and sibs)
Early onset: ≤15 years.
Alcoholism: Patients had alcohol use disorder during the BPI course.
Psychosis: Patients had delusions and/or hallucinations during manic and depressive episodes.
Rapid cycling: Patients had at least four episodes of manic, depressive, or hypomanic episodes in the last 12 months.
Gender: males

TABLE 11

Genetic factor contributing to response to lithium prophylaxis treatment among bipolar 1 patients (N = 394) in the presence of rs17026688: Logistic regression model *

| dbSNP RS# | Chromosome | Position | P value** |
|---|---|---|---|
| rs1158454 | 3 | 30830280 | 0.007 |
| rs1910333 | 3 | 30832232 | 0.705 |
| rs17026628 | 3 | 30832324 | 0.031 |
| rs869484 | 3 | 30838465 | 0.280 |
| rs17026642 | 3 | 30844064 | 0.043 |
| rs17026643 | 3 | 30845750 | 0.687 |
| rs1494730 | 3 | 30846244 | 0.623 |
| rs6780262 | 3 | 30846680 | 0.865 |
| rs1494731 | 3 | 30846903 | 0.884 |
| rs6771562 | 3 | 30846936 | 0.014 |
| rs1494732 | 3 | 30847081 | 0.884 |
| rs13318432 | 3 | 30848144 | 0.288 |
| rs2220850 | 3 | 30848648 | 0.014 |
| rs1353275 | 3 | 30848764 | 0.873 |
| rs1389908 | 3 | 30853295 | 0.070 |
| rs931557 | 3 | 30854776 | 0.151 |
| rs11709194 | 3 | 30859293 | 0.577 |
| rs6792186 | 3 | 30867723 | 0.213 |
| rs7652680 | 3 | 30872827 | 0.338 |
| rs6775621 | 3 | 30878650 | 0.301 |
| rs4955342 | 3 | 30878747 | 0.205 |
| rs4955346 | 3 | 30879119 | 0.338 |
| rs4521277 | 3 | 30879801 | 0.338 |
| rs4955348 | 3 | 30879848 | 0.362 |
| rs1389903 | 3 | 30880388 | 0.338 |
| rs7641301 | 3 | 30881421 | 0.356 |
| rs9842693 | 3 | 30885556 | 0.338 |

* Logit (responder) = SNP + rs17026688 + Family history + Early onset + Alcoholism + Psychosis + Rapid cycling + Gender, where the variables were coded as 1 for the following definition and 0 for others:
Responders with a total score in Alda Scale from 6 to 10
SNP: the carriers of effect allele at the SNP
Rs17026688: the carriers of effective allele T
Family history: BPI in first-degree relatives (parents, children and sibs)
Early onset: ≤15 years.
Alcoholism: Patients had alcohol use disorder during the BPI course.
Psychosis: Patients had delusions and hallucinations during manic and depressive episodes.
Rapid cycling: Patients had at least four episodes of manic, depressive, or hypomanic episodes in the last 12 months.
Gender: male.
**All P values were not significant (<0.00185 = 0.05/26) after Bonferroni correction for multiple comparisons.

TABLE 12

Variants identified in GADL1 by direct sequencing.

| Variant | Region | Position (GRCh36) | Position (GRCh37) | Nucleic acid change | Amino acid change | Genotype | Frequency Responder (%) | Frequency Non-responder (%) | PCR primer |
|---|---|---|---|---|---|---|---|---|---|
| rs149015569 | Promoter | 3:30912809 | 3:30937805 | C > T | | CC:CT:TT | 96.8:3.2:0 | 100.0:0:0 | F: TTCCTAGGGCTTTCATTCTCA (SEQ ID NO: 6) |
| c.-1678 | Promoter | 3:30912788 | 3:30937784 | G > A | | GG:GA:AA | 98.9:1.1:0 | 100.0:0:0 | R: TTCACATCGGTGAAGACAGG (SEQ ID NO: 7) |
| c.-1610 | Promoter | 3:30912720 | 3:30937716 | T > C | | TT:TC:CC | 98.9:1.1:0 | 100.0:0:0 | |
| c.-1461 | Promoter | 3:30912571 | 3:30937567 | G > A | | GG:GA:AA | 100.0:0:0 | 98.9:1.1:0 | |
| rs145854215 | Promoter | 3:30912531 | 3:30937527 | C > T | | CC:CT:TT | 96.8:3.2:0 | 100.0:0:0 | |
| rs57701574 | Promoter | 3:30912512 | 3:30937508 | C > G | | CC:CG:GG | 26.6:51.1:22.3 | 40.4:43.6:16.0 | |
| c.-1339 | Promoter | 3:30912449 | 3:30937445 | C > T | | CC:CT:TT | 26.6:51.1:22.3 | 40.4:44.7:14.9 | F: AGGATGTTCGCATGATGGAT (SEQ ID NO: 8) |
| c.-1207 | Promoter | 3:30912317 | 3:30937313 | G > C | | GG:GC:CC | 98.9:1.1:0 | 100.0:0:0 | R: CGGCATTTTGTCATTCCTC (SEQ ID NO: 9) |
| rs141038985 | Promoter | 3:30912262 | 3:30937258 | C > T | | CC:CT:TT | 98.9:1.1:0 | 100.0:0:0 | |
| c.-12 | 5' UTR | 3:30911122 | 3:30936118 | G > T | | GG:GT:TT | 97.9:2.1:0 | 97.9:2.1:0 | F: CCAAATTACCCACGCTCCTA (SEQ ID NO: 10) |
| c.-8 | 5' UTR | 3:30911118 | 3:30936114 | G > C | | GG:GC:CC | 98.9:1.1:0 | 100.0:0:0 | R: CCAGCCGCTTTACAAAGAAA (SEQ ID NO: 11) |
| c.31 | Exon1 | 3:30911080 | 3:30936076 | G > C | V11L | GG:GC:CC | 98.9:1.1:0 | 100.0:0:0 | |
| IVS1+14 | Intron1 | 3:30911058 | 3:30936054 | G > A | | GG:GA:AA | 98.9:1.1:0 | 100.0:0:0 | |
| rs6774917 | Intron2 | 3:30878012 | 3:30903008 | G > A | | GG:GA:AA | 47.9:43.6:8.5 | 19.2:45.7:35.1 | F: GCCATCTGAAGCTGGATAG (SEQ ID NO: 12) R:GCCTGAAGGACAGCCTACAC (SEQ ID NO: 13) |
| rs141606916 | Intron3 | 3:30873463-30873465 | 3:30898459-30898461 | CTT del | | ins/ins:ins/-:-/- | 62.8:33.0:4.2 | 80.9:19.1:0 | F: GCCCAGAAGCTTTGTAATGG (SEQ ID NO: 14) R: TTATCTTTGGCCTTGCAAT (SEQ ID NO: 15) |
| IVS4-86 | Intron4 | 3:30867523 | 3:30892519 | T > G | | TT:TG:GG | 97.9:2.1:0 | 96.8:3.2:0 | F: GCCACAAGCTATTGGCATTT (SEQ ID NO: 16) R: TCTGCAAGGAGTTGTTCCTC (SEQ ID NO: 17) |
| c.554 | Exon6 | 3:30866589 | 3:30891585 | T > C | M185T | TT:TC:CC | 100.0:0:0 | 97.9:2.1:0 | F AATAATGGAGCAGGAGGT (SEQ ID NO: 18) |
| c.577 | Exon6 | 3:30866566 | 3:30891562 | T > C | Y193H | TT:TC:CC | 97.9:2.1:0 | 100.0:0:0 | R: AAATTGGACCAGGCGTTACA (SEQ ID NO: 19) |
| c.615 | Exon6 | 3:30866528 | 3:30891524 | T > A | S205S | TT:TA:AA | 98.9:1.1:0 | 98.9:1.1:0 | |
| c.617 | Exon6 | 3:30866526 | 3:30891522 | G > T | G206V | GG:GT:TT | 98.9:1.1:0 | 98.9:1.1:0 | |
| rs1494738 | Intron7 | 3:30860810 | 3:30883806 | G > A | | GG:GA:AA | 61.7:34.0:4.3 | 31.9:50.0:18.1 | F: AATGTCCAAAGATTGTGCT (SEQ ID NO: 20) |
| IVS8+41_44 | Intron8 | 3:30860662-3:30860665 | 3:30885658-3:30885661 | TGTG del | | ins/ins:ins/-:-/- | 100.0:0:0 | 98.9:1.1:0 | R:TCTCTCCACACATAGAAATGG (SEQ ID NO: 21) |
| IVS8+48 | Intron8 | 3:30860658 | 3:30885654 | G del | | 00:0/-:-/- | 16.0:56.4:27.6 | 87.2:12.8:0 | |
| c.797 | Exon9 | 3:30855599 | 3:30880595 | C > T | P266L | CC:CT:TT | 98.9:1.1:0 | 98.9:1.1:0 | F: ATGCCAAGAGGCCACATATT (SEQ ID NO: 22) |
| rs115154257 | Exon9 | 3:30855522 | 3:30880518 | G > A | E292K | GG:GA:AA | 94.7:5.3:0 | 98.9:1.1:0 | R: TTTCCCCAATTTGAGACAC |

TABLE 12-continued

Variants identified in GADL1 by direct sequencing.

| Variant | Region | Position (GRCh36) | Position (GRCh37) | Nucleic acid change | Amino acid change | Genotype | Frequency Responder (%) | Non-responder (%) | PCR primer |
|---|---|---|---|---|---|---|---|---|---|
| rs6550024 | Intron12 | 3:30802908 | 3:30827904 | T > C | | TT:TC:CC | 8.5:57.5:34.0 | 31.9:45.8:22.3 | F: CTCAGGCCAAGGAAATTACAG (SEQ ID NO: 23) |
| IVS13+93 | Intron13 | 3:30802758 | 3:30827754 | G > C | | GG:GC:CC | 100.0:0:0 | 98.9:1.1:0 | (SEQ ID NO: 24) |
| rs58010707 | Intron13 | 3:30802729 | 3:30827725 | C > T | | CC:CT:TT | 19.2:58.5:22.3 | 69.1:27.7:3.2 | R: TCTGTGAATCCAACAAGGAAA (SEQ ID NO: 25) |
| rs35503213 | Intron13 | 3:30794836-30794837 | 3:30819832-30819833 | AG del | | ins/ins:ins/-:-/- | 15.0:61.2:23.8 | 63.8:31.9:4.3 | F: AAGAAGGCAGAAGGGATTGTT (SEQ ID NO: 26) |
| rs1157799 | Intron13 | 3:30794769 | 3:30819765 | C > A | | CC:CA:AA | 97.5:2.5:0 | 95.7:4.3:0 | R: CTGTTTGGCCTGICATTACTIT (SEQ ID NO: 27) |
| rs11278928 | Intron14 | 3:30794667-30794673 | 3:30819663-30819669 | TAAGTAA del | | ins/ins:ins/-:-/- | 81.3:17.5:1.2 | 52.2:36.2:11.6 | |
| rs12054099 | Intron14 | 3:30744935 | 3:3076993 | C > T | | CC:CT:TT | 46.8:45.7:7.5 | 62.8:30.8:6.4 | F: GAATGGGATCCAAACCAGTG (SEQ ID NO: 28) R: AGTCCAGGGACCACACTTTG (SEQ ID NO: 29) | c. = cDNA sequence,
c. + 1 is the ATG-translation initiation codon, the nucleotide 5' of the ATG-translation initiation codon is c.-1

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. A method of detecting a glutamate decarboxylase-like 1 (GADL1) gene variant in a bipolar disorder patient, the method comprising:
   obtaining a sample from a patient having bipolar disorder; and
   assaying the sample to detect one or more GADL1 gene variants selected from the group consisting of:
   (i) a T allele of the single nucleotide polymorphism (SNP) rs17026688;
   (ii) a G allele of the SNP rs17026651; and
   (iii) GADL1 IVS8+48delG.

2. The method of claim 1, wherein the sample is a genomic DNA sample.

3. The method of claim 1, wherein the sample is an RNA sample.

4. The method of claim 1, wherein the sample is obtained from the blood or saliva of the patient.

5. The method of claim 1, wherein the assaying step is performed by DNA sequencing, restriction enzyme digest, polymerase chain reaction (PCR), hybridization, real-time PCR, reverse transcriptase PCR, or ligase chain reaction.

6. The method of claim 1, wherein the patient is a bipolar disorder I patient of self reported Han Chinese descent.

7. A method of treating bipolar disorder in a subject, the method comprising:
   obtaining a sample from a patient having bipolar disorder;
   assaying the sample to detect one or more glutamate decarboxylase-like 1 (GADL1) gene variants, the variants being selected from the group consisting of:
   (i) a T allele of the single nucleotide polymorphism (SNP) rs17026688;
   (ii) a G allele of the SNP rs17026651; and
   (iii) GADL1 IVS8+48delG; and
   administering lithium treatment to the patient.

8. The method of claim 7, wherein the sample is a genomic DNA sample.

9. The method of claim 7, wherein the sample is an RNA sample.

10. The method of claim 7, wherein the sample is obtained from the blood or saliva of the patient.

11. The method of claim 7, wherein the assaying step is performed by sequencing, restriction enzyme digest, polymerase chain reaction (PCR), hybridization, real-time PCR, reverse transcriptase PCR, or ligase chain reaction.

12. The method of claim 7, wherein the patient is a bipolar disorder I patient of self reported Han Chinese descent.

* * * * *